(12) United States Patent
Taneja et al.

(10) Patent No.: US 9,636,390 B2
(45) Date of Patent: May 2, 2017

(54) IMMUNOGENIC ANTIGENS OF SHIGELLA

(71) Applicants: Indian Council of Medical Research, New Delhi (IN); Post-Graduate Institute of Medical Education and Research (PGIMER), Chandigarth (IN)

(72) Inventors: Neelam Taneja, Chandigarh (IN); Sapna Pahil, Chandigarh (IN); Meera Sharma, Chandigarh (IN)

(73) Assignees: Indian Council of Medical Research, New Delhi (IN); Post Graduate Institute of Medical Education and Research (PGIMER), Chandigarh (IN)

( * ) Notice: Subject to any disclaimer, the term of this patent is extended or adjusted under 35 U.S.C. 154(b) by 11 days.

(21) Appl. No.: 14/443,555

(22) PCT Filed: Nov. 19, 2013

(86) PCT No.: PCT/IN2013/000703
§ 371 (c)(1),
(2) Date: May 18, 2015

(87) PCT Pub. No.: WO2014/076714
PCT Pub. Date: May 22, 2014

(65) Prior Publication Data
US 2015/0283223 A1    Oct. 8, 2015

(30) Foreign Application Priority Data

Nov. 19, 2012 (IN) .......................... 3543/DEL/2012

(51) Int. Cl.
A61K 35/74     (2015.01)
A61K 39/112    (2006.01)
A61K 39/00     (2006.01)

(52) U.S. Cl.
CPC ..... *A61K 39/0283* (2013.01); *A61K 2039/55566* (2013.01)

(58) Field of Classification Search
CPC .. A61K 35/74; A61K 38/16; A61K 39/55516; A61K 39/0283; A61K 48/00; C12Q 1/689
See application file for complete search history.

(56) References Cited

U.S. PATENT DOCUMENTS

2002/0172685 A1* 11/2002 Stewart .................. A61K 39/04
424/190.1

FOREIGN PATENT DOCUMENTS

WO    2011/036564 A2    3/2011

OTHER PUBLICATIONS

Chitradevi et al., (Vaccine 2013. 12;31(16):2035-41).*
Barry et al. "Immunogenicity of multivalent Shigella-ETEC candidate vaccine strains in a guinea pig model" Vaccine 24 (18): 3727-3734 (2006).

* cited by examiner

*Primary Examiner* — Ja'na Hines
(74) *Attorney, Agent, or Firm* — The Webb Law Firm

(57) ABSTRACT

A vaccine for protection against multiple serotypes of *Shigella* sp., comprising a putative heat shock protein (EL PGI II), and Hypothetical Protein (EL PGIV) is provided.

5 Claims, 9 Drawing Sheets

Figure 1:
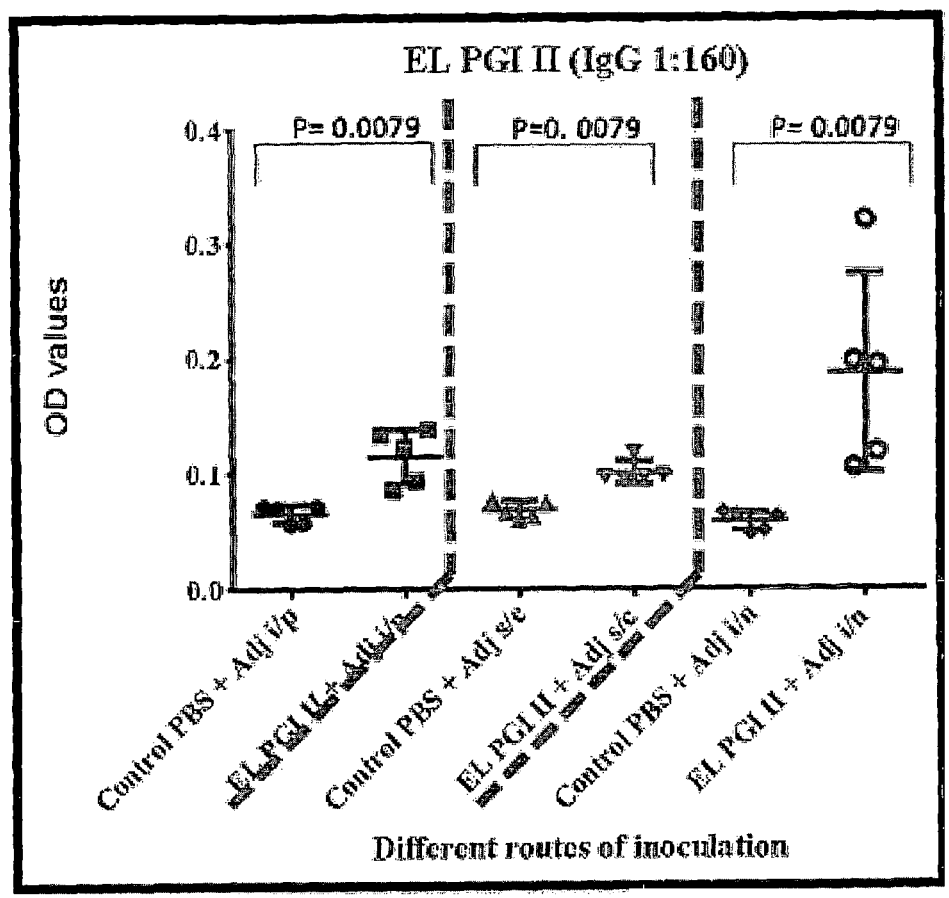

1. Putative heat shock protein(EL PGI II) - size 28 KDa

>gi|82777568|ref|YP_403917.1| putative heat shock protein [Shigella dysenteriae Sd197]
MINQRMIHMKNTKLLLAIATSAALLTGCQNTHGIDTNMAISSGLNAY
KAATLSDADAKAIANQGCAEMDS
GNQVASKSSKYGKRLAKIAKALGNNINGTPVNYKVYMTSDVNAWA
MANGCVRVYSGLMDMMNDNEIEGVL
GHELGHVALGHSLAEMKASYAIVAARDAISATSGVASQLSRSQLGDI
AEGAINAKYSRDKESEADDFSFD
LLKKRGISTQGLVGSFEKLASLDGGRTQSMFDSHPPSTERAQHIRDRI
ASGK
Peptide synthesized - DSGNQVASKSSKYGK

2. Hypothetical Protein (EL PGI V) - Size 28 KDa
>gi|30062956|ref|NP_837127.1| hypothetical protein S1556 [Shigella flexneri 2a str. 2457T]
MTKLKLLALGVLIATSAGVAHAEGKFSLGAGVGVVEHPYKDYDTD
VYPVPVINYEGDNFWFRGLGGGYYL
WNDATDKLSITAYWSPLYFKAKDSGDHQMRHLDDRKSTMMAGLS
YAHFTQYGYLRTTLAGDTLDNSNGIV
WDMAWLYRYTNGGLTVTPGIGVQWNSENQNEYYYGVSRKESARS
GLRGYNPNDSWSPYLELSASYNFLGD
WSVYGTARYTRLSDEVTDSPMVDKSWTGLISTGITYKF
Peptide synthesized − YGVSRKESARSGLRGYN

Fig 9

SEQUENCE LISTING

<160> NUMBER OF SEQ ID NOS: 4

<210> SEQ ID NO 1
<211> LENGTH: 262
<212> TYPE: PRT
<213> ORGANISM: Shigella flexneri

<400> SEQUENCE: 1

Met Ile Asn Gln Arg Met Ile His Met Lys Asn Thr Lys Leu Leu Leu
1               5                   10                  15

```
Ala Ile Ala Thr Ser Ala Ala Leu Leu Thr Gly Cys Gln Asn Thr His
            20                  25                  30

Gly Ile Asp Thr Asn Met Ala Ile Ser Ser Gly Leu Asn Ala Tyr Lys
        35                  40                  45

Ala Ala Thr Leu Ser Asp Ala Asp Ala Lys Ala Ile Ala Asn Gln Gly
    50                  55                  60

Cys Ala Glu Met Asp Ser Gly Asn Gln Val Ala Ser Lys Ser Ser Lys
65                  70                  75                  80

Tyr Gly Lys Arg Leu Ala Lys Ile Ala Lys Ala Leu Gly Asn Asn Ile
                85                  90                  95

Asn Gly Thr Pro Val Asn Tyr Lys Val Tyr Met Thr Ser Asp Val Asn
            100                 105                 110

Ala Trp Ala Met Ala Asn Gly Cys Val Arg Val Tyr Ser Gly Leu Met
        115                 120                 125

Asp Met Met Asn Asp Asn Glu Ile Glu Gly Val Leu Gly His Glu Leu
    130                 135                 140

Gly His Val Ala Leu Gly His Ser Leu Ala Glu Met Lys Ala Ser Tyr
145                 150                 155                 160

Ala Ile Val Ala Ala Arg Asp Ala Ile Ser Ala Thr Ser Gly Val Ala
                165                 170                 175

Ser Gln Leu Ser Arg Ser Gln Leu Gly Asp Ile Ala Glu Gly Ala Ile
            180                 185                 190

Asn Ala Lys Tyr Ser Arg Asp Lys Glu Ser Glu Ala Asp Asp Phe Ser
        195                 200                 205

Phe Asp Leu Leu Lys Lys Arg Gly Ile Ser Thr Gln Gly Leu Val Gly
    210                 215                 220

Ser Phe Glu Lys Leu Ala Ser Leu Asp Gly Gly Arg Thr Gln Ser Met
225                 230                 235                 240

Phe Asp Ser His Pro Pro Ser Thr Glu Arg Ala Gln His Ile Arg Asp
                245                 250                 255

Arg Ile Ala Ser Gly Lys
            260

<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Asp Ser Gly Asn Gln Val Ala Ser Lys Ser Ser Lys Tyr Gly Lys
1               5                   10                  15

<210> SEQ ID NO 3
<211> LENGTH: 247
<212> TYPE: PRT
<213> ORGANISM: Shigella flexneri

<400> SEQUENCE: 3

Met Thr Lys Leu Lys Leu Leu Ala Leu Gly Val Leu Ile Ala Thr Ser
1               5                   10                  15

Ala Gly Val Ala His Ala Glu Gly Lys Phe Ser Leu Gly Ala Gly Val
            20                  25                  30

Gly Val Val Glu His Pro Tyr Lys Asp Tyr Asp Thr Asp Val Tyr Pro
        35                  40                  45

Val Pro Val Ile Asn Tyr Glu Gly Asp Asn Phe Trp Phe Arg Gly Leu
```

```
                50                  55                  60
Gly Gly Gly Tyr Tyr Leu Trp Asn Asp Ala Thr Asp Lys Leu Ser Ile
 65                  70                  75                  80

Thr Ala Tyr Trp Ser Pro Leu Tyr Phe Lys Ala Lys Asp Ser Gly Asp
                 85                  90                  95

His Gln Met Arg His Leu Asp Asp Arg Lys Ser Thr Met Met Ala Gly
                100                 105                 110

Leu Ser Tyr Ala His Phe Thr Gln Tyr Gly Tyr Leu Arg Thr Thr Leu
                115                 120                 125

Ala Gly Asp Thr Leu Asp Asn Ser Asn Gly Ile Val Trp Asp Met Ala
                130                 135                 140

Trp Leu Tyr Arg Tyr Thr Asn Gly Gly Leu Thr Val Thr Pro Gly Ile
145                 150                 155                 160

Gly Val Gln Trp Asn Ser Glu Asn Gln Asn Glu Tyr Tyr Tyr Gly Val
                165                 170                 175

Ser Arg Lys Glu Ser Ala Arg Ser Gly Leu Arg Gly Tyr Asn Pro Asn
                180                 185                 190

Asp Ser Trp Ser Pro Tyr Leu Glu Leu Ser Ala Ser Tyr Phe Leu Gly
                195                 200                 205

Asp Trp Ser Val Tyr Gly Thr Ala Arg Tyr Thr Arg Leu Ser Asp Glu
                210                 215                 220

Val Thr Asp Ser Pro Met Val Asp Lys Ser Trp Thr Gly Leu Ile Ser
225                 230                 235                 240

Thr Gly Ile Thr Tyr Lys Phe
                245

<210> SEQ ID NO 4
<211> LENGTH: 17
<212> TYPE: PRT
<213> ORGANISM: Artificial Sequence
<220> FEATURE:
<223> OTHER INFORMATION: synthetic peptide

<400> SEQUENCE: 4

Tyr Gly Val Ser Arg Lys Glu Ser Ala Arg Ser Gly Leu Arg Gly Tyr
 1               5                  10                  15

Asn
```

US 9,636,390 B2

IMMUNOGENIC ANTIGENS OF SHIGELLA

CROSS-REFERENCE TO RELATED APPLICATIONS

This application is the United States national phase of International Application No. PCT/IN2013/000703 filed Nov. 19, 2013, and claims priority to Indian Patent Application No. 3543/DEL/2012 filed Nov. 19, 2012, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 154579_ST25.txt. The size of the text file is 5,368 bytes, and the text file was created on May 15, 2015.

FIELD OF THE INVENTION

This invention relates to novel immunogenic protein antigens that are common to Shigella spp. and the use of these antigens either as vaccine candidates or in developing sero-diagnostic test for identification of Shigella. This invention also discloses means and methods for identifying immunogenic Shigella antigens. The invention further discloses amino acid sequences of these immunogenic proteins and synthetic peptide sequences used in the study which are capable of eliciting immune response in Balb/c mice and also with human sera.

BACKGROUND OF THE INVENTION

Shigellosis is a leading cause of bacillary dysentery in humans. Each year, over 163 million cases occur worldwide, with the majority of cases occurring in children in developing countries, and 0.0 million cases resulting in death. Antibiotics are generally effective against shigellosis, but because Shigellae are increasingly developing antibiotic resistance, even to the newest antibiotics, the World Health Organization has given priority to the development of a safe and effective vaccine against Shigella.

Four Shigella species (or groups) are now recognized: S. dysenteriae (group A), which has 15 serotypes; Shigella flexneri (group B), which has 14 classical serotypes and subserotypes; Shigella boydii (group C), which has 20 serotypes; and Shigella sonnei (group D), which has a single serotype. The target populations for the use of Shigella vaccines include infants and young children in developing countries (in whom the peak incidence occurs at 12-47 months of age and the S. flexneri serotypes predominate). S. Dysenteriae 1, which produces Shiga toxin and typically carries R factors that encode resistance to multiple antibiotics, causes epidemics of this disease worldwide.

S. sonnei persists in developed (and transitional) countries, causing sporadic diarrhea and occasional outbreaks in epidemiological niches. Travelers from developed to developing regions, who mainly acquire S. sonnei and S. flexneri infections, represent another target population for Shigella vaccines. Consequently, a Shigella vaccine that can provide a high level of protection against S. dysenteriae 1, all S. flexneri serotypes and S. sonnei would constitute an epidemiological valid 'global' vaccine but to include such large number of serotypes is not feasible. Three main serotypes, S. Sonnei, S. flexneri 2a and S. flexneri 6, caused 79% of the cases of shigellosis so a combination of these three with epidemic dysentery causing S. dysenteriae 1 wall serve the purpose.

Convincing evidence that an initial clinical Shigella infection elicits serotype-homologous protection comes from three sources: NHP challenge studies, volunteer model re-challenge studies and prospective epidemiological surveillance of a cohort of children in an endemic area. Many approaches have been used for Shigella vaccines such as live attenuated, killed whole bacteria, Shigella LPS or O-polysaccharide conjugated to carriers such as proteosomes, tetanus toxoid and ribosomes. Inspite of extensive research for so many years an effective Shigella vaccine is still not available and the greatest impediment to achieving a useful Shigella vaccine is devising a strategy that can confer broad protection against a large number of epidemiologically relevant serotypes.

OBJECTS OF THE INVENTION

It is therefore an object of this invention to propose novel immunogenic protein antigens that are common to Shigella spp, for development of Shigella Vaccine which confers broad protection against a large number of epidemiologically relevant serotypes.

It is a further object of this invention to propose novel immunogenic protein antigens that are common to Shigella spp for development of Shigella Vaccine, which is effective.

Another object of this invention is to propose novel immunogenic protein antigens that are common to Shigella spp, for use in immuno-diagnosis of Shigella.

These and other objects and advantages of the invention will be apparent from the ensuing description.

BRIEF DESCRIPTION OF THE ACCOMPANYING DRAWINGS

FIG. 1: Titres of IgG antibody (1:160) in BALB/c mice against the putative heat shock protein (EL PGI II) antigen inoculated by three different routes: (i/p, s/c and i/n); (P value<0.05 i/p, s/c, i/n)

Figure 2:
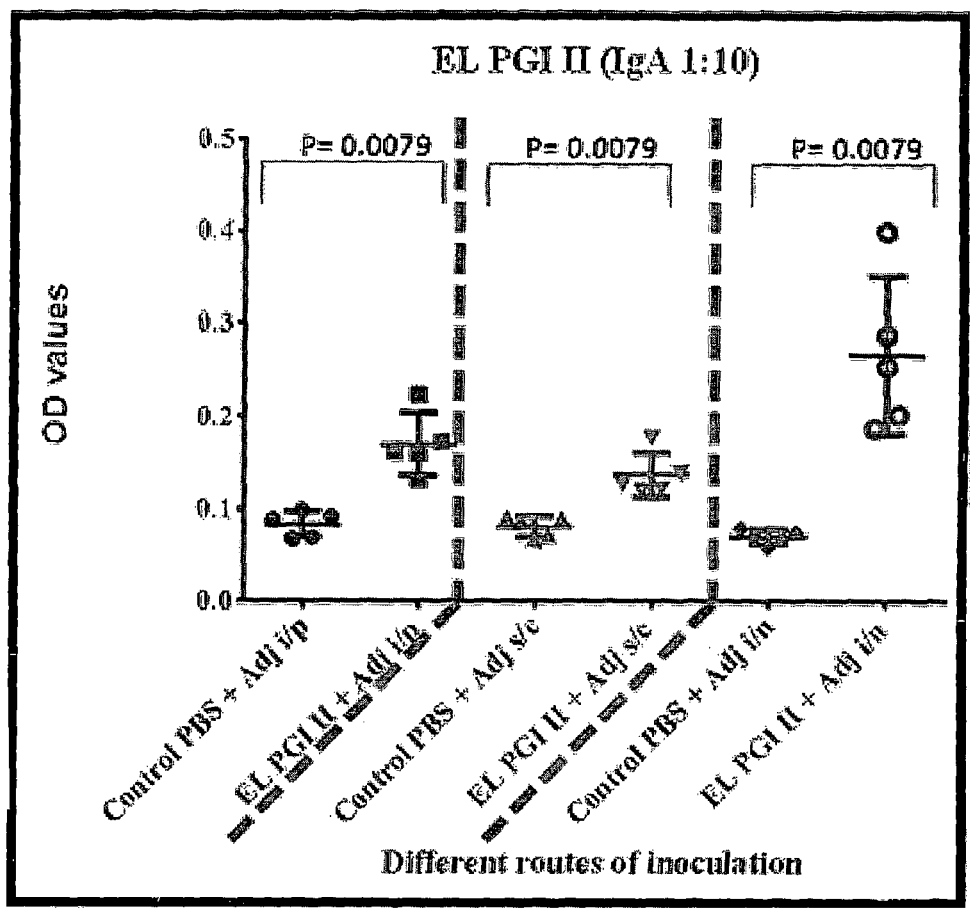

FIG. 2: Titres of IgA antibody (1:10) in BALB/c mice against the putative heat shock protein (EL PGI II) antigen inoculated by three different routes: (i/p, s/c and i/n); (P value<0.05 i/p, s/c, i/n)

Figure 3:
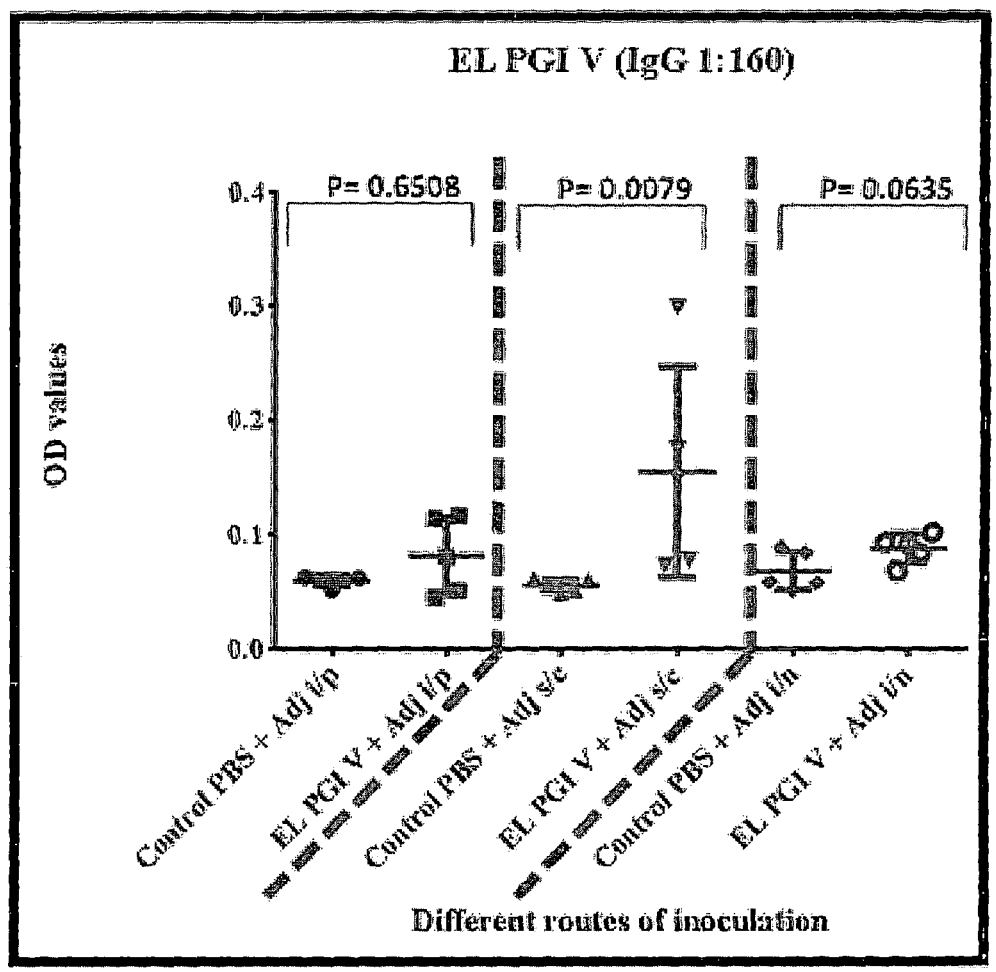

FIG. 3: Titres of IgG antibody (1:160) in BALB/c mice against the putative hypothetical protein (EL PGI V) antigen inoculated by three different routes: (i/p, s/c and i/n); (P value>0.05 i/p, i/n; P value<0.05 s/c)

Figure 4:
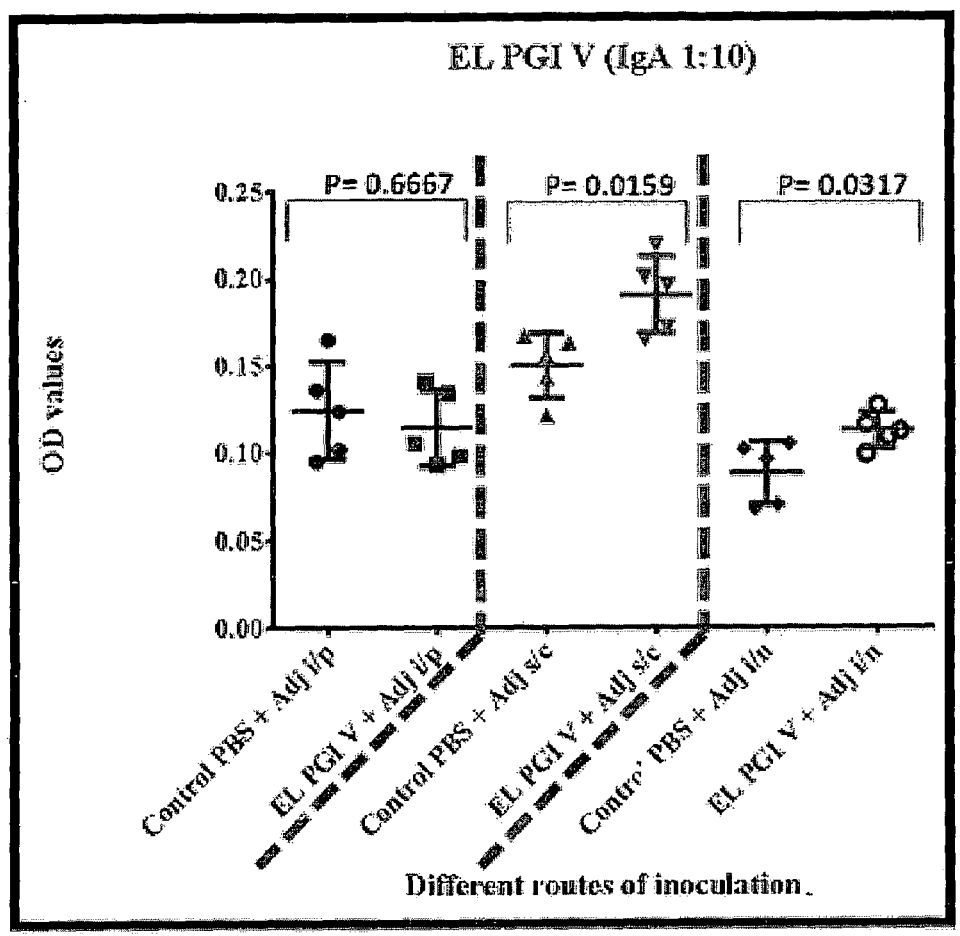

FIG. 4: Titres of IgA antibody (1:10) in BALB/c mice against the putative hypothetical protein (EL PGI V) antigen inoculated by three different routes: (i/p, s/c and i/n); (P value>0.05 i/p; P value<0.05 s/c, i/n)

Figure 5:
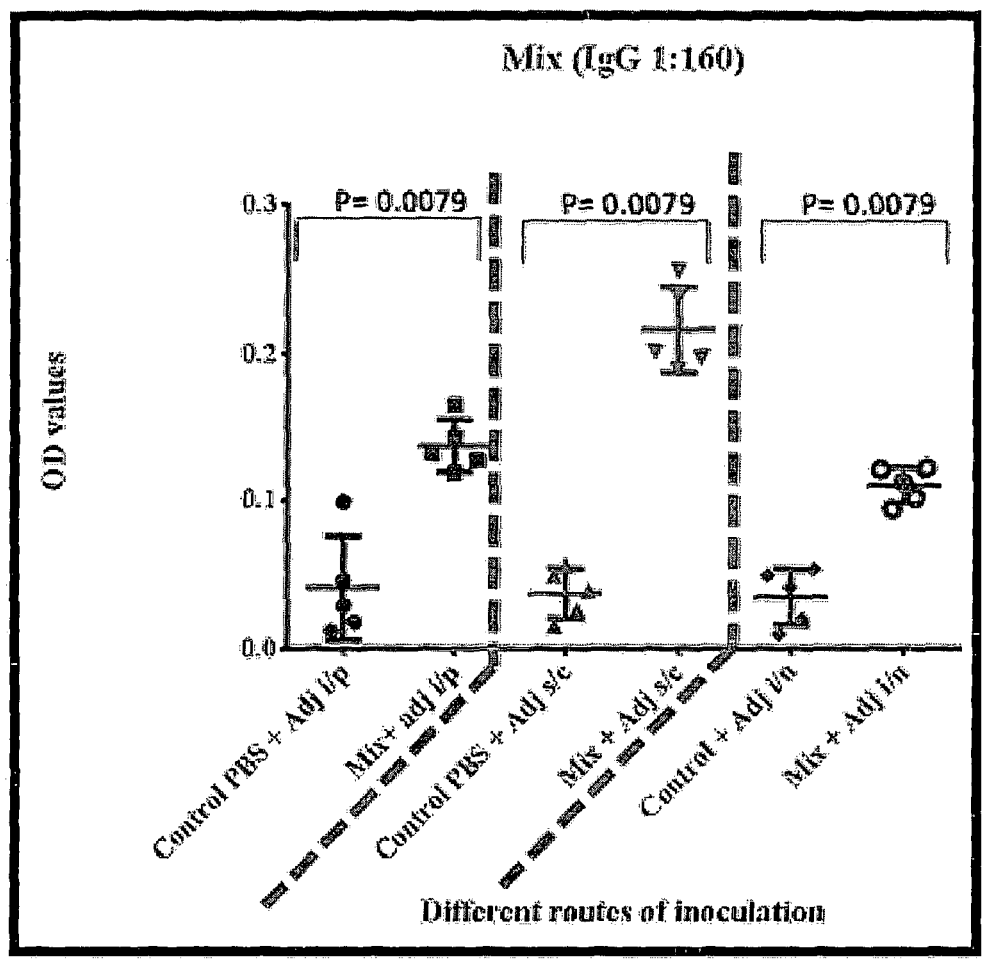
Figure 6:
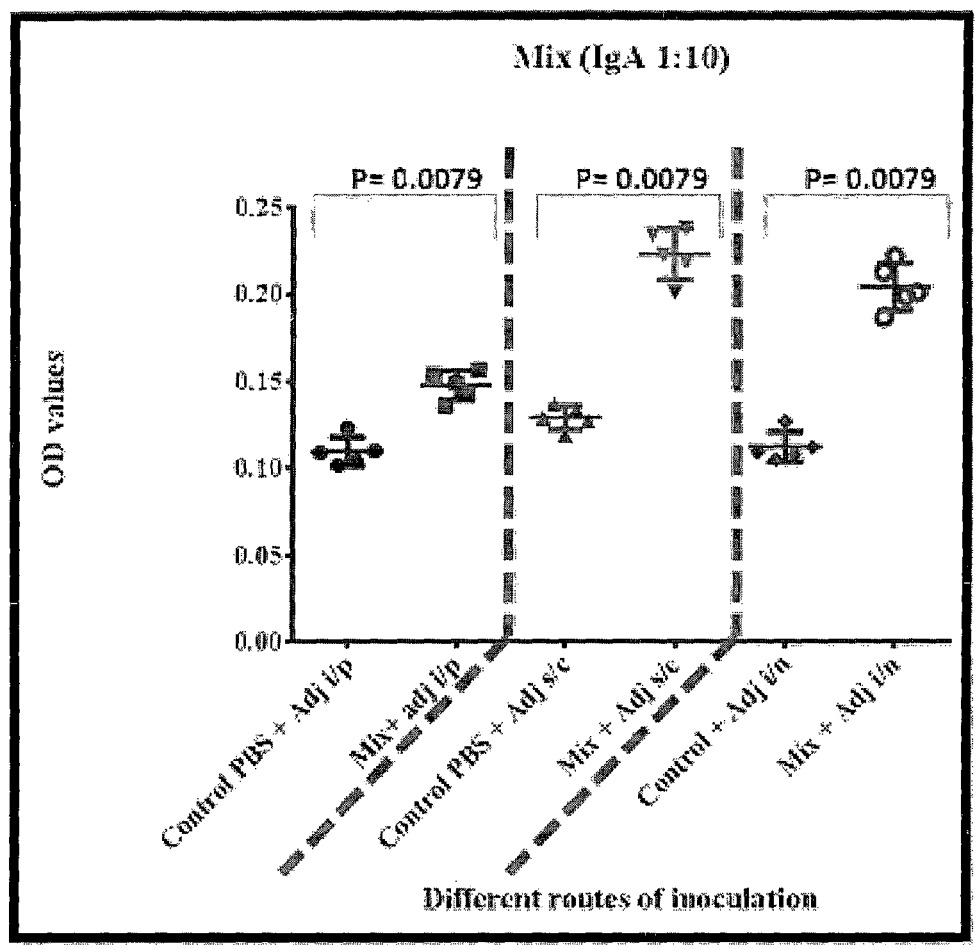
Figure 7:
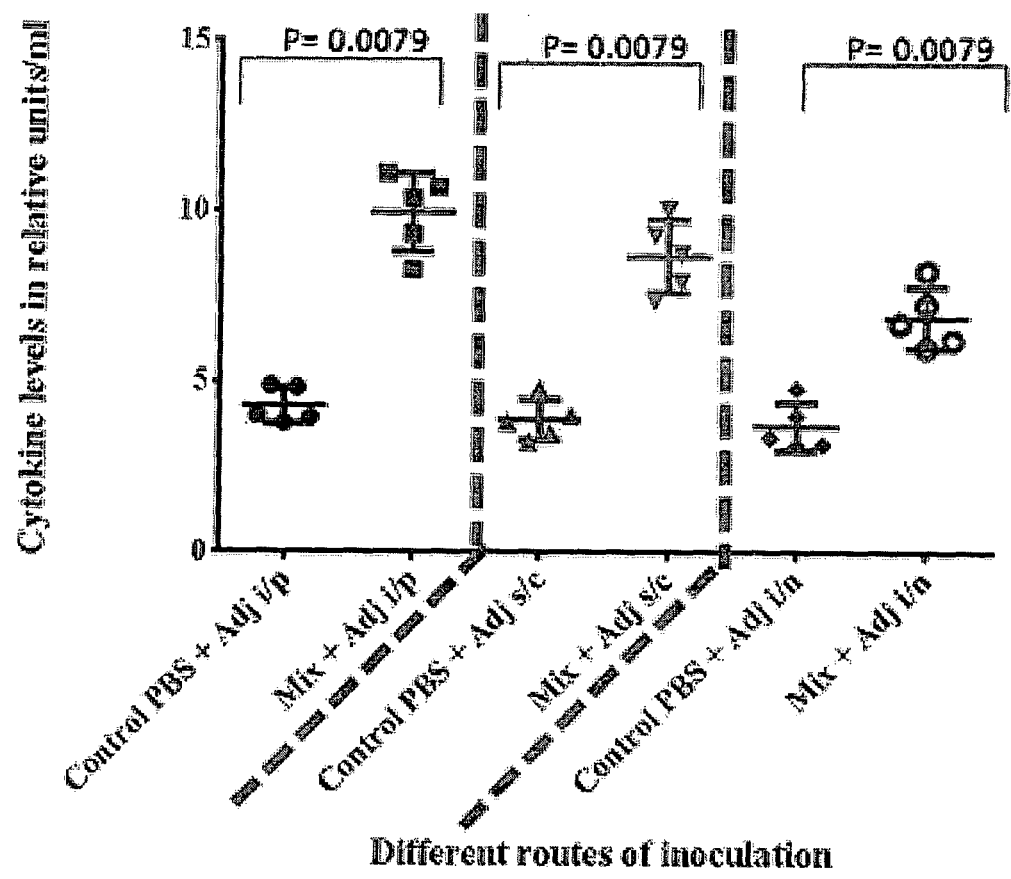
Figure 8:
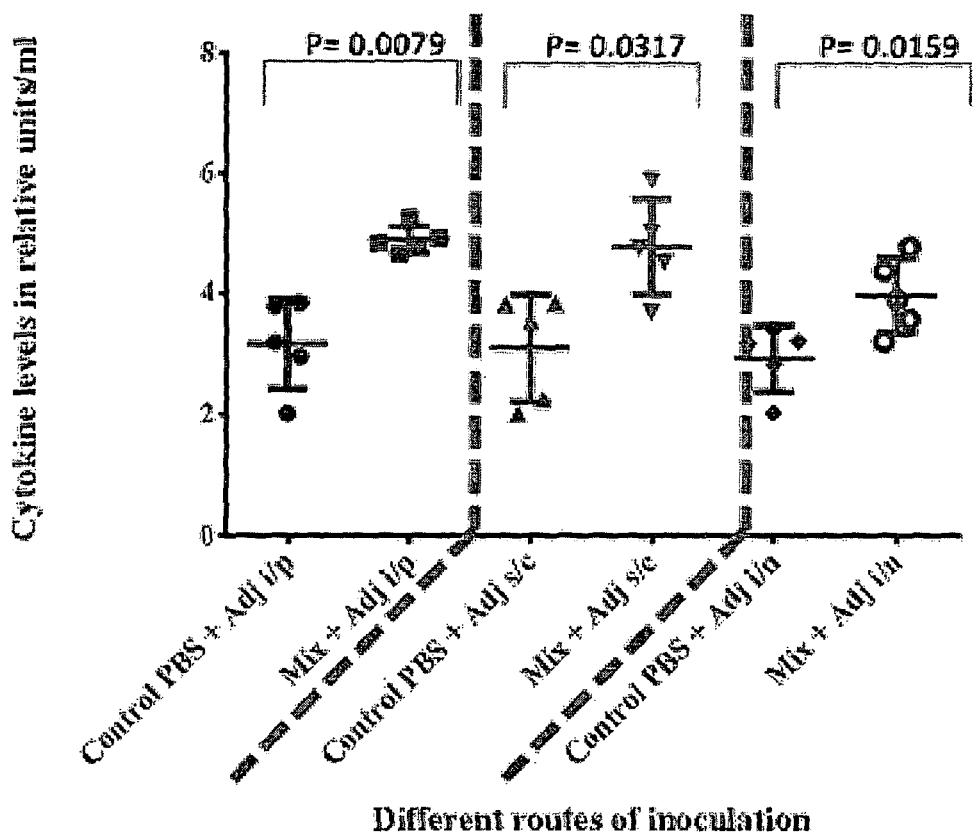

FIG. 5: Results with mixture of peptides: mixture produced significant IgG response by all three routes FIG. 6: Results with mixture of peptides: Mixture produced significant IgA response by all routes FIG. 7: Results of TNF alpha with mixture of peptides: Mixture produced significant TNF alpha response by all routes FIG. 8: Results of IFN gamma with mixture of peptides: the mixture was found to produce significant IFN gamma response by all routes FIG. 9: Sequence IDs of peptides and amino acids EL PGI II (full length peptide—SEQ ID NO: 1; synthesized peptide—SEQ ID NO: 2), and EL PGI V (full length peptide—SEQ ID NO: 3; synthesized peptide—SEQ ID NO: 4).

DETAILED DESCRIPTION OF THE INVENTION

Thus according to this invention is provided novel immunogenic protein antigens for use in preparing vaccines or developing sero-diagnostic test for identification of *Shigella*.

According to this invention is further provided a vaccine for protection against multiple serotypes of *Shigella* sp.

In accordance with this invention, the complete proteome databases of most common serotypes of *Shigella* (*S dysenteriae* serotype 1, *S sonnei, S flexneri* 2a) have been searched on NCBI and a local database of approx 17,000 proteins has been made. Then protein BLAST has been performed on selected database to find proteins common in most prevalent serotypes such as *S. dysenteriae* serotype 1, *S. sonnei* and *S. Flexneri* 2a.

After BLAST, 7038 proteins were obtained and for all these proteins, protein localization prediction has been done.

After this localization study, those proteins were targeted which are either secreted out or are present on the surface of the bacterium as immune response is generated against these proteins when infection occurs as these proteins come in contact with host cells. 250 outer-membrane or secreted proteins were obtained and epitope prediction for 250 selected proteins was done. B-cell epitope prediction, T-cell epitope prediction and MHC binding score was done for all proteins so that highly immunogenic proteins could be selected for further use.

Finally 48 peptides which have B-cell and T-cell epitopes and MHC binding properties were arrived at. Out of these, 5 peptides (putative lipoprotein (EL PGI I), putative heat shock protein (EL PGI II), Spa32 (EL PGI III), IcsB (EL PGI IV), and hypothetical protein (EL PGI V)) were artificially synthesized which had maximum MHC binding score. Immunogenicity of these peptides was checked in BALB/c mice and human sera of patients suffering from shigellosis. The antibody response was checked by ELISA and T-cell response by cytokine analysis.

Artificial Peptide Synthesis

Five peptides which were immunodominant by in-silico analysis were artificially synthesized from USV (United States Vitamins Ltd., Mumbai, India). These peptides were of more than 95% purity. We describe the peptides (ELPGI-II and ELPGI-V) that have been filed for the patent and are identified by their sequences below:

```
1. Putative heat shock protein(EL PGI II) - size 28 KDa
>gi|82777568|ref|YP_403917.1 | putative heat shock protein [Shigella
dysenteriae Sd197]
MINQRMIHMKNTKLLLAIATSAALLTGCQNTHGIDTNMAISSGLNAYKAATLSDADAKAIANQGCAEMDS

GNQVASKSSKYGKRLAKIAKALGNNINGTPVNYKVYMTSDVNAWAMANGCVRVYSGLMDMMNDNEIEGVL

GHELGHVALGHSLAEMKASYAIVAARDAISATSGVASQLSRSQLGDIAEGAINAKYSRDKESEADDFSFD

LLKKRGISTQGLVGSFEKLASLDGGRTQSMFDSHPPSTERAQHIRDRIASGK (SEQ ID NO: 1)

Peptide synthesized - DSGNQVASKSSKYGK (SEQ ID NO: 2)

2. Hypothetical Protein (EL PGI V) - Size 28 KDa
>gi|30062956|ref|NP_837127.1|hypothetical protein SI 556 [Shigella
flexneri 2a str. 2457T]
MTKLKLLALGVLIATSAGVAHAEGKFSLGAGVGVVEHPYKDYDTDVYPVPVINYEGDNFWFRGLGGGYYL

WNDATDKLSITAYWSPLYFKAKDSGDHQMRHLDDRKSTMMAGLSYAHFTQYGYLRTTLAGDTLDNSNGIV

WDMAWLYRYTNGGLTVTPGIGVQWNSENQNEYYYGVSRKESARSGLRGYNPNDSWSPYLELSASYNFLGD

WSVYGTARYTRLSDEVTDSPMVDKSWTGLISTGITYKF (SEQ ID NO: 3)

Peptide synthesized - YGVSRKESARSGLRGYN (SEQ ID NO: 4)
```

FIG. 9: sequence ID.

Immunogenicity Check of Selected Peptides in Balb/c Mice

| Mice used | Intraperitoneal (i/p) route | Subcutaneous (s/c) route | Intranasal (i/n) | Dosing Schedule |
|---|---|---|---|---|
| Female Balb/c | Control PBS only | Control PBS only | Control PBS only | 3 doses at two weeks interval |
| Female Balb/c | Control PBS + adjuvant | Control PBS + adjuvant | Control PBS + adjuvant | 3 doses at two weeks interval 1$^{st}$ dose with CFA and subsequent with IFA |
| Female Balb/c | Test group = Peptide + adjuvant | Test group = Peptide + adjuvant | Test group = Peptide + adjuvant | 3 doses at two weeks interval 1$^{st}$ dose with CFA and subsequent with IFA |

6 weeks old female Balb/c Mice were taken and divided into three groups
  i.e one for intraperitoneal injections (i/p) another for subcutaneous injections(s/c) and yet another for intranasal (i/n) route. Five mice were used in each group for one antigen, two groups of control and one group test (15 mice used per antigen). The Schedule is shown in Table 1 above.
Dosing Schedule:
  Three groups of 6 weeks old female balb/c mice were taken. Each group i/p, s/c were or i/n divided into subgroups of control and test. Two types of control were used in the study, PBS only (Phosphate buffer saline) and second control of PBS+ adjuvant. Test group were given peptide with adjuvant. First dose was given with CFA (Freund's complete adjuvant) and two subsequent doses were given with IFA (incomplete Freund's adjuvant). Three doses were given at two weeks interval and after three weeks of last dose blood was collected from mice by retro-orbital plexus. Serum was stored at −20° C. and −80° C. for ELISA and Cytokine analysis respectively.
Collection of Human Patient Sera:
  Sera was collected from 15 patients who were suffering from dysentery and who were culture positive for *Shigella*. Both IgG and IgA ELISA were performed for these sera with the same peptide antigens used for injecting the mouse.

2) Next morning the antigen coated plate was washed thrice with washing buffer PBST (Phosphate buffer saline with 0.02% tween 20)
3) 2% bovine serum albumin (BSA, 100 µl) was added to each well to block the remaining unbound sites on the plate. Plate was incubated at 37° C. for 1 hour and was washed thrice with washing buffer.
4) Test and control sera was diluted in PBST to optimum dilution and 1000 of dilution was added to appropriate labelled wells of micro titer plate and was incubated at 37° C. for 1 hour.
5) After washing with PBST 100 µl of enzyme labelled anti-mouse IgG horse radish peroxidise (HRP) conjugate (Sigma-Aldrich), diluted as 1:10,000 (optimum dilution will be added to each well. The plate was incubated at 37° C. for 1 hour.
6) This was followed by washing thrice with PBST and 100 µl of ortho phenylene diamine (OPD) and $H_2O_2$ was added in each well as substrate in dark. The plate was kept at room temperature for 15 minutes in dark.
7) The reaction was stopped with 1M $H_2SO_4$ and absorbance was read with ELISA reader at 490 nm.
  Similarly IgA antibody was detected by ELISA after checker board titration.

TABLE 2

Results of ELISA and Cytokine analysis:

| Peptide Name | Mouse antibody and cytokine | Human antibody response |
|---|---|---|
| putative lipoprotein (EL PGI I) | IgA (i/p), TNFα, IFNγ | Negative |
| putative heat shock protein (EL PGI II) | IgG, IgA and TNFα by all three routes | IgG and IgA (Very good response) |
| Spa32 (EL PGI III) | TNFα, IFNγ | Negative |
| IcsB (EL PGI IV) | IgA (only by S/c route) and TNFα, IFNγ | IgG and IgA in some patients |
| hypothetical protein (EL PGI V) | IgG, IgA and TNFα by all three routes | IgG and IgA (Very good response) |

Cytokines Assay
  Cytokine analysis was done by Flow cytometry using BD Biosciences Ltd. India, mouse Th1 and Th2 cytokine kit. Serum samples stored at −80° C. were processed according to manufacture's instructions. Cytokine assays were performed for both Th1 and Th2 cytokines (TNFα, IFNγ, IL-4, IL-1, and IL-10).
Enzyme-Linked Immunosorbent Assay (ELISA)
Protocol for In-House Indirect ELISA for Detection of Antibody IgG & IgA against Selected Synthetic Peptides:
  The antibody detection (IgG and IgA) was done by micro ELISA technique. Optimum antigen dilution (10 µg/well), used for coating the wells of the micro-titer plates was determined by checker board titration method. The optimum serum dilutions of the test samples (1:20, 1:40, 1:80 for IgG. and 1:5, 1:10, 1:20 for IgA) which were used were determined in the same way using various dilution of known positive and negative sera with plates coated with optimum dilution of antigen. ELISA was carried out according to the standard technique with certain modifications wherever required. The steps followed were as follows:
  1) One hundred micro liter of antigen diluted in coating buffer (10 µg/well) was used for coating the well of micro-titer plate and the plate was kept at 4° C. overnight covered with tin foil and ELISA plate cover, so as to minimize evaporation.

Out of these five tested antigens, either humoral or cytokine response was seen in all the antigens, whereas except spa32 (EL PGI III), four antigens showed both antibody and cytokine response in Balb/c mice. Two antigens putative heat shock protein (EL PGI II), IcsB (EL PGI IV) and hypothetical protein (EL PGI V)) came out to be very promising. The results are depicted in the FIGS. 1-8
  The results are summed up as follows (Table 3 shows for the ELPGI-II and ELPGI-V)

TABLE 3

| Peptide | Route | IgG | IgA | TNF | INF |
|---|---|---|---|---|---|
| (ELPGI-2) | Ip | Y | Y | Y | |
| | Sc | Y | Y | | |
| | In | Y | Y | | |
| (ELPGI-5) | ip | | | Y | |
| | sc | Y | Y | Y | |
| | in | Y | Y | Y | |
| Mix | ip | Y | Y | Y | Y |
| | sc | Y | Y | Y | Y |
| | in | Y | Y | Y | Y |

Y: Yes

The antigens showed antibody response with human sera of patients suffering from shigellosis. This shows these antigens are immunogenic for humans also. Discovery of these immunodominant antigens common to major serotypes of Shigella (S dysenteriae serotype 1, S sonnei, S flexner Ua) is of further immunodiagnostic importance for diagnosis of Shigella and serves as a vaccine candidate.

These two antigens, putative heat shock protein (EL PGI II), and hypothetical protein (EL PGI V) which are immunogenic in Balb/c mice and with human sera of patients suffering from shigellosis are novel immunogenic antigens as they are common to multiple serotypes of Shigella. The immune response of these antigens against Shigella spp. Has been tested. Serotype specific immunity is a major drawback for vaccine development against Shigella till now so these three antigens have overcome this aspect also. So this finding can be of great importance in future for developing serodiagnostic test for identification of Shigella or for developing an effective vaccine against multiple serotypes of Shigella. Amino acid sequences of whole proteins as well as sequences of synthetic peptides of these immunogenic antigens used in this invention are shown in FIG. 9. Overall these documents does not exist any patent relating to these novel common immunogenic antigens against Shigella spp.

The results are being described for the EL PGI II & EL PGI V antigens only. They were found to be immunogenic by the intranasal route also (FIG. 1-8 and Table 3, 4)

Human Experiment Data
Collection of Human Patient Sera 15 patients sera who were suffering from dysentery and who were culture positive for Shigella.
  Both IgG and IgA ELISA were performed for these sera with the same peptide antigens used for injecting the mouse.
  Same number of age and sex matched healthy controls were also selected who did not suffer from diarrhea in past six months
  The results are highlighted in Table 4

TABLE 4

| Patient no. | Age in years & sex | Days of diarrhoea/ dysentery | EL PGI II IgG | EL PGI II IgA | EL PGI V IgG | EL PGI V IgA |
|---|---|---|---|---|---|---|
| 1. | 5/F | 5-6 | +ve | +ve | +ve | +ve |
| 2. | 45/M | 6-7 | +ve | +ve | +ve | +ve |
| 3. | 65/M | 10 | +ve | +ve | -ve | -ve |
| 4. | 41/M | Chronic diarrhoea | -ve | +ve | -ve | +ve |
| 5. (BMT) | 54/M | 6 | -ve | +ve | +ve | +ve |
| 6. | 28/M | 10 | +ve | +ve | -ve | -ve |
| 7. (HIV +ve) | 50/M | Chronic diarrhoea | -ve | -ve | +ve | +ve |
| 8. | 63/F | Chronic diarrhoea | +ve | +ve | -ve | +ve |
| 9. | 57/M | 7-8 | +ve | +ve | +ve | +ve |
| 10. | 1/M | 8 | +ve | -ve | -ve | +ve |
| 11. | 14/M | 7 | +ve | +ve | +ve | |
| 12. | 14/M | 7-8 | -ve | +ve | +ve | +ve |
| 13. (Renal transplant) | 40/M | 6 | -ve | +ve | -ve | +ve |
| 14. | 2/F | 5-6 | +ve | -ve | -ve | -ve |
| 15. | 45/M | 5-6 | -ve | +ve | +ve | +ve |

ELPGI II IgA antibody response in 12/15 patients
ELPGI V IgA antibody response in 11/15 patients
Therefore protective antibodies are present in human sera against these antigens Table 5 shows the cytokine responses in these patient sera: As can be seen IL-1beta, IL-10, TNFalpha and IFN gamma responses were significant

TABLE 5

| | Control samples | | | | | |
|---|---|---|---|---|---|---|
| sample no. | IL-1β | IL-2 | IL-4 | IL-10 | TNF-α | IFN-γ |
| 1 | 17.23 | 19.05 | 16.99 | 12.89 | 20.76 | 23.09 |
| 2 | 12.68 | 5.09 | 20.99 | 68.09 | 11.98 | 23.34 |
| 3 | 12.23 | 37.9 | 17.21 | 9.89 | 12.67 | 22.02 |
| 4 | 9.76 | 8.09 | 19.89 | 45.9 | 11.9 | 21.89 |
| 5 | 5.64 | 12.9 | 23.98 | 58.23 | 18.09 | 27.83 |
| 6 | 14.73 | 11.56 | 1.58 | 22.9 | 12.23 | 24.45 |
| 7 | 21.89 | 1.34 | 45.02 | 27.74 | 12.67 | 10.98 |
| 8 | 27.83 | 17.34 | 32.23 | 11.12 | 11.99 | 22.87 |
| 9 | 24.45 | 2.9 | 23.87 | 11.91 | 12.9 | 23.83 |
| 10 | 10.98 | 9.02 | 11.87 | 33.9 | 23.81 | 35.68 |
| 11 | 21.76 | 17.09 | 15.23 | 15.44 | 18.82 | 21.19 |
| 12 | 19.01 | 26.01 | 1.89 | 20.04 | 21.09 | 27.23 |
| 13 | 8.04 | 5.08 | 12.01 | 28.78 | 18.89 | 24.45 |
| 14 | 14.71 | 17.98 | 19.23 | 12.09 | 18.02 | 22.9 |
| 15 | 9.86 | 28.02 | 11.89 | 34.9 | 15.05 | 15.84 |
| P value | 0.03 Significant | 0.15 NS | 0.82 NS | 0.017 Significant | 0.0004 Significant | 0.0001 Significant |
| S. no. 1 | 2.98 | 8.19 | 11.9 | 12 | 12.09 | 2.89 |
| 2 | 8.34 | 2.98 | 8.01 | 8.72 | 3.78 | 15.91 |
| 3 | 12.08 | 11.56 | 40 | 2.04 | 1.98 | 3.98 |
| 4 | 10.78 | 1.34 | 9.87 | 7.78 | 2.98 | 12.12 |
| 5 | 15.93 | 17.39 | 23.9 | 11.09 | 8.34 | 13.72 |
| 6 | 12.09 | 2.9 | 18.33 | 4.9 | 12.08 | 11.28 |
| 7 | 4.01 | 9.02 | 11 | 19.02 | 10.78 | 10.34 |
| 8 | 7.9 | 17.09 | 23.01 | 20.9 | 15.93 | 8.45 |
| 9 | 2.87 | 6.01 | 12 | 22.9 | 12.09 | 18.72 |
| 10 | 18.9 | 5.08 | 45.9 | 20.4 | 4.01 | 15.64 |
| 11 | 12.87 | 17.98 | 19.809 | 10.74 | 7.9 | 10.38 |
| 12 | 10.8105 | 8.02 | 10.60106 | 9.62 | 8.9 | 3.98 |

We claim:

1. A method of inducing an immune response in an organism, comprising administering to the organism an immunogenic amount of an immunogenic composition comprising a putative heat shock protein having the sequence consisting of SEQ ID NO: 1 and/or SEQ ID NO: 2, and a hypothetical protein having the sequence consisting of SEQ ID NO: 3 and/or SEQ ID NO: 4.

2. A method of detecting the presence of antibodies against *Shigella* in a sample obtained from an organism comprising:
   contacting a sample derived from the blood of an organism suspected of being infected by *Shigella* with a protein comprising a putative heat shock protein and a hypothetical protein; and detecting binding of the protein to one or more antibodies against *Shigella*.

3. The method of claim 2, wherein the putative heat shock protein has the sequence of SEQ. ID No: 1 and the hypothetical protein has the sequence of SEQ. ID No: 3.

4. The method of claim 1, wherein the composition is administered at least twice, and wherein a first dose includes an adjuvant including inactivated mycobacteria, and wherein a second dose includes an adjuvant that does not include an inactivated mycobacteria.

5. The method of claim 2, where the detecting step comprises use of an immunosorbent assay.

* * * * *

UNITED STATES PATENT AND TRADEMARK OFFICE
CERTIFICATE OF CORRECTION

PATENT NO. : 9,636,390 B2  
APPLICATION NO. : 14/443555  
DATED : May 2, 2017  
INVENTOR(S) : Neelam Taneja et al.

Page 1 of 1

It is certified that error appears in the above-identified patent and that said Letters Patent is hereby corrected as shown below:

On the Title Page

In (71) Column 1, Line 4, delete "Chandigarth," and insert -- Chandigarh, --

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*